United States Patent [19]

Kluender

[11] 4,159,998

[45] Jul. 3, 1979

[54] PROCESS FOR THE PREPARATION OF 2-(7-HYDROXYALKYL)-4R, 4S OR 4RS -HYDROXY-CYCLOPENT-2-ENONE

[75] Inventor: Harold C. Kluender, Madison, Wis.

[73] Assignee: Miles Laboratories, Inc., Elkhart, Ind.

[21] Appl. No.: 940,977

[22] Filed: Sep. 11, 1978

[51] Int. Cl.$^2$ .............................................. C07C 45/00
[52] U.S. Cl. ............................ 260/586 R; 260/456 P; 560/106; 560/121; 568/667
[58] Field of Search ........................... 260/586, 456 P; 560/106, 121; 568/667

[56] References Cited

U.S. PATENT DOCUMENTS 3,773,622  11/1973  Sih .................................... 195/51 R

OTHER PUBLICATIONS

Kluender et al., Tetra. Letters, No. 24, p. 2063 (1977).
Sih et al., "J.A.C.S.", vol. 95, p. 1676 (1973).
Sih et al., "J.A.C.S.", vol. 96, p. 865, (1975).

Primary Examiner—Norman Morgenstern
Attorney, Agent, or Firm—Jerome L. Jeffers

[57] ABSTRACT

Disclosed is an improved process for the preparation of 2-(7-hydroxyalkyl)-4R, 4S or 4RS -hydroxy-cyclopent-2-enone corresponding to the formula

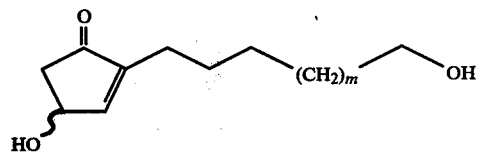

wherein m is an integer from 2 to 4.

The compounds prepared by this process are useful as precursors in the preparation of carbinol PGE$_1$ analogues having utility as bronchodilators and inhibitors of gastric secretion.

25 Claims, No Drawings

PROCESS FOR THE PREPARATION OF 2-(7-HYDROXYALKYL)-4R, 4S OR 4RS -HYDROXY-CYCLOPENT-2-ENONE

BACKGROUND OF THE INVENTION

Natural prostaglandins are alicyclic compounds related to prostanoic acid, the structure of which is:

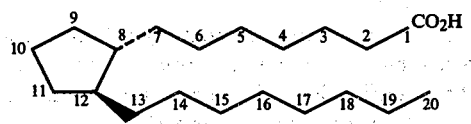

By convention, the carbon atoms of prostanoic acid are numbered sequentially from the carboxylic carbon atom. An important stereo-chemical feature of this compound is the trans-orientation of the $C_1$–$C_7$ and $C_{13}$–$C_{20}$ sidechains, which orientation is common to all natural prostaglandins. In prostanoic acid, as elsewhere in this specification, solid lines (—) provide a reference plane (such as the cyclopentyl ring or the bonds between atoms $C_1$–$C_7$ and $C_{13}$–$C_{20}$; a dashed line (- - -) indicates projection of a covalent bond below the reference plane (alpha-configuration); while a wedged line (◂) represents orientation above the reference plane (beta-configuration). In some structures, however, a swung dash or serpentine line (~) denotes orientation of a covalent bond either above or below the plane of reference (indicated by the Greek letter xi in the nomenclature of such structure).

Natural prostaglandins have the general structure,

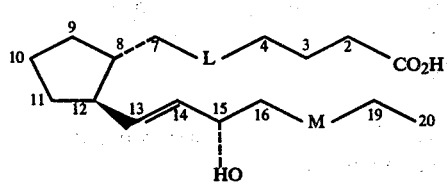

in which L and M may be ethylene or cis-vinylene radicals. When the cyclopentyl ring is substituted with a carbonyl group at the 9 position and an alpha hydroxyl group at the 11 position, i.e.,

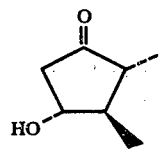

an important type of prostaglandin known as the E-class is depicted.

The above formula for natural prostaglandins and the representation of the cyclopentyl moiety depict the nat-isomer, i.e., the $C_7$–$C_8$ bond in the alpha configuration and the $C_{12}$–$C_{13}$ bond in the beta-configuration. In the ent-isomer (which does not occur in nature), the direction of the bonds at $C_7$–$C_8$ and $C_{12}$–$C_{13}$ is reversed.

When L and M in the foregoing formula are ethylene (as opposed to cis-vinylene) there is only a trans-double bond at the ($C_{13}$–$C_{14}$ position and such a prostaglandin is known as type 1. Then there is a carbonyl moiety at $C_9$ and an alpha-hydroxyl moiety at $C_{11}$ with a trans-double bond at $C_{13}$–$C_{14}$, i.e.,

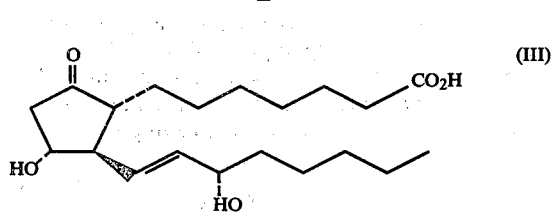

the prostaglandin is known as $PGE_1$ or $11\alpha$, 15S-dihydroxy-9-oxoprost-13E-en-1-oic acid.

Naturally occurring $PGE_1$ or synthetic analogues thereof elicit biochemical and physiological effects in a variety of mammalian systems. For example, in rats $PGE_1$ increases the release of growth hormone while in sheep it inhibits ovarian progesterone secretion. In mice, $PGE_1$ increases thyroid activity whereas in hypophysectomized rats it stimulates stereoidogenesis in the adrenal glands. In general PGE compounds relax in vitro human uterine muscle strips, and $PGE_1$ has been found to inhibit gastric secretion.

It has been found that PGE compounds may, in the respiratory area, prove beneficial in the therapy of bronchial asthma and other diseases involving bronchoconstriction due to their bronchodilatory effect. In this regard carbinol analogues of $PGE_1$, i.e., those in which the —COOH group at the 1-position is converted to a —$CH_2OH$ group, have shown great potential as antiasthma agents. For example, U.S. Pat. No. 4,022,912 issued on May 10, 1977 discloses that 1, $11\alpha$, 15S-trihydroxyprost-13E-en-9-one of the formula:

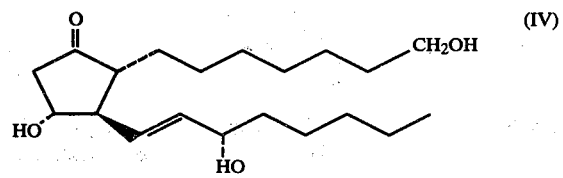

is an excellent bronchodilator which is much more effective in this regard than naturally occurring $PGE_1$.

Carbinol derivatives of $PGE_1$ also possess great potential as anti-ulcer agents due to their demonstrated activity in inhibiting gastric secretion in an individual for whom such therapy is indicated. Thus, 1,11,15-trihydroxy-16,20-methano analogues of $PGE_1$, having the general structural formula:

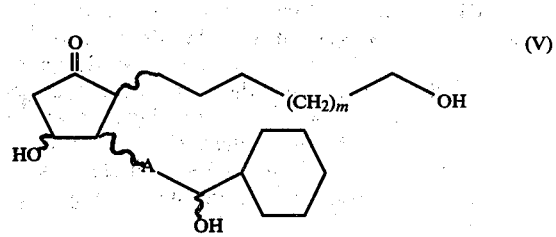

wherein m is an integer of from 2 to 4, and A is an ethylene or vinylene radical are useful in this regard. These compounds are prepared by reacting an organolithiocuprate of the formula:

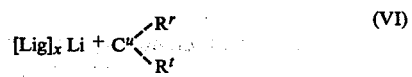

in which Lig is tri-(di-alkylamino)phosphine of 6–12 carbon atoms, trialkylphosphine having 3–12 carbon atoms, diarylphosphine, dialkylsulfide having 2–8 carbon atoms, arylsulfide, or di-(trialkylsilyl)amino having 6–12 carbon atoms; $R^t$ is a radical having the formula:

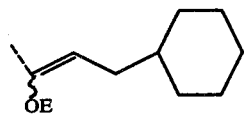
(VII)

wherein and subsequently elsewhere E is tetrahydropyran-2-yl, trialkylsilyl having 3 to 12 carbon atoms, triarylsilyl, alkoxy-alkyl having 2–6 carbon atoms, or triarylmethyl; $R^r$ is iodide, thiophenylate, alkyn-1-yl having 3 to 8 carbon atoms, or $R^t$; and x is an integer of the set 0–4 provided that x is 0 only when $R^r$ is thiophenylate; with a 2-(ω-hydroxyalkyl)-4R,4S or 4RS-hydroxycyclopent-2-enone of the formula:

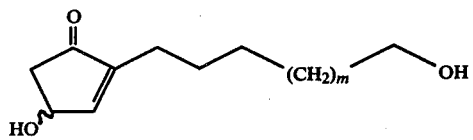
(VIII)

to obtain a carbinol analogue of $PGE_1$ having the formula:

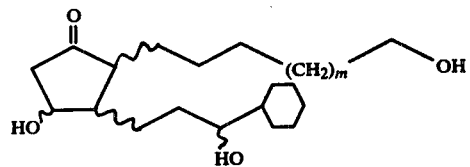
(VIII)

which can subsequently be hydrogenated to yield the carbinol analogue of PGE in which A is ethylene, i.e.,

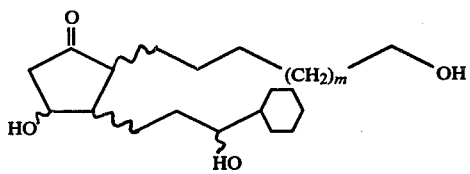
(X)

The substituted cyclopent-2-en-1-one set out in formula VIII is an essential intermediate in the formation of the carbinol analogues of formulae IV, IX and X.

Typically the substituted cyclopent-2-en-1-one set out in formula VIII (in which the ring hydroxyl has the R configuration) is prepared from ethyl 9-oxodecanoate as described in *Tetrahedron Letters*, 2063 (1977). Thus, ethyl 9-oxodecanoate is converted in four steps as described to the intermediate substituted cyclopentan-1,3,4-trione of the formula:

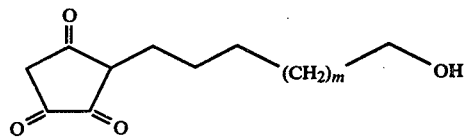
(XI)

wherein m is 3; and then intermediate XI is treated with an aqueous culture of an appropriate microorganism such as *Dipodascus uninucleatus* as disclosed in U.S. Pat. No. 3,773,622 to yield after exhaustive extraction of the beer, a very polar product of the formula:

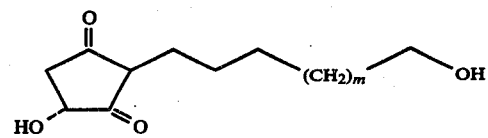
(XI-A)

which is usually contaminated with other fermentation products and must therefore be purified by chromatography. The purified XI-A is then converted in three steps to an intermediate of structure VIII.

According to a process described in *J. Amer. Chem. Soc.*, 95, 1676 (1973) alkyl 9-oxodecanoate is converted in one step to a product of the formula:

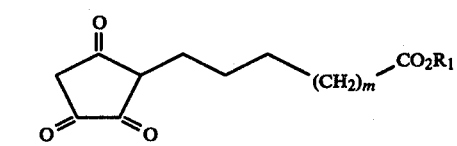
(XI-B)

wherein m is 3 and $R_1$ is an alkyl group containing from 1 to 4 carbon atoms; and then intermediate XI according to U.S. Pat. No. 3,773,622 is converted by contact with appropriate microorganisms to a product of the formula:

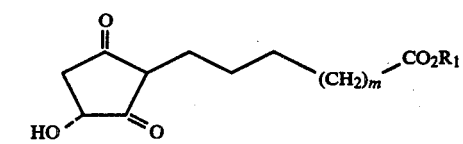
(XI-C)

wherein m and $R_1$ are as defined above, in good yields without chromatography.

The S compound represented by the formula:

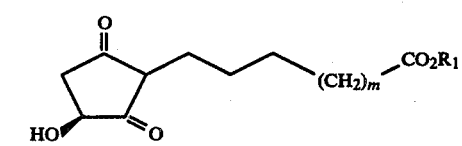
(XI-D)

is prepared as described in *J. Amer. Chem. Soc.*, 97, 865 (1975) and the RS material, i.e., (XI-E)

is prepared as described in *Ann. N.Y. Acad. Sci.*, 180, 64 (1971).

SUMMARY OF THE INVENTION

The present invention is an improved process for the preparation of 2-(ω-hydroxyalkyl)-4R,4S or 4RS-hydroxy-cyclopent-2-enone corresponding to the formula:

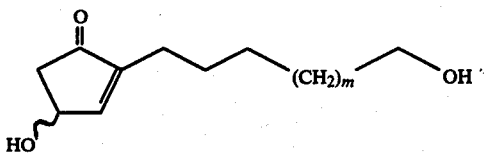

wherein m is an integer of from 2 to 4, which process comprises the steps of:

A. reacting in an inert solvent under a dry atmosphere a 2-(ω-carboalkoxyalkyl-4R,4S or 4RS-hydroxycyclopentan-1,3-dione corresponding to the formula:

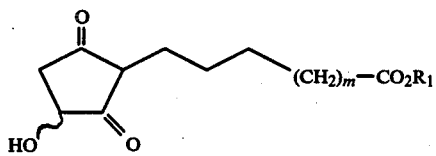

wherein m is an integer of from 2 to 4 and $R_1$ is an alkyl group containing from 1 to 4 carbon atoms, with mesitylenesulfonyl chloride, a lower alkyliodide of from 1 to 4 carbon atoms or benzoyl chloride in the presence of an excess of a tertiary or aromatic amine to convert the starting material to the corresponding enol sulfonate, enol ether or enol benzoate;

B. reacting in an inert solvent and under an inert atmosphere the so-formed enol sulfonate, enol ether or enol benzoate with an excess of a metallic hydride reducing agent capable of reducing the ester and carbonyl groups on the enol sulfonate, ether or benzoate to primary and secondary alcohol groups respectively, at a temperature not in excess of about 35° C. to reduce the carbonyl group on the starting material to a hydroxyl group and to reduce the ester group on the starting material to an alcohol group to thereby form an intermediate material corresponding to the formula:

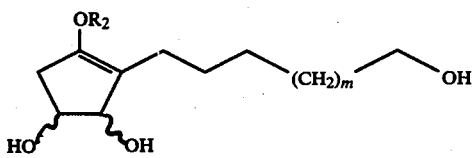

wherein $R_2$ is mesitylenesulfonyl, lower alkyl of 1 to 4 carbon atoms or benzoyl and m is an integer from 2 to 4;

C. adding a dilute aqueous solution of a mineral acid and a water immiscible organic solvent to the reaction mass to convert unreacted amine to its corresponding amine salt and cause the amine salt to reside in the so-formed aqueous phase and cause the intermediate material formed in step B to reside in the so-formed organic phase;

D. separating the aqueous phase from the organic phase;

E. washing the organic phase with an aqueous base to remove the acid therefrom;

F. separating the intermediate material formed in step B from the organic phase; and G. dissolving the intermediate material in chloroform, methylene chloride, a lower alcohol or a mixture thereof and reacting it with sodium oxalate and oxalic acid to form the desired product.

The present invention represents an improvement over the prior art because fewer steps are necessary in the preparation of VIII from ethyl 9-oxodecanoate using the new process (5 steps) than are necessary in the old process (8 steps). Also, the fermentation step in the new process is easier to conduct than the same reaction in the prior art process because the products of the new process are purer as directly obtained from that step.

DETAILED DESCRIPTION AND PREFERRED EMBODIMENTS

The initial step of the process of the instant invention involves reacting, in an inert solvent and under a dry atmosphere a 2-(ω-carboalkoxyalkyl)-4R,4S or 4RS-hydroxycyclopentan-1,3-dione prepared as previously described with mesitylenesulfonyl chloride, a lower alkyliodide or benzoyl chloride in the presence of an excess of a tertiary or aromatic amine. This step converts the starting material to the corresponding enol sulfonate, enol ether or enol benzoate. Typical of inert solvents, i.e., those solvents which are non-reactive with the starting materials or the products, are diethyl ether, tetrahydrofuran and p-dioxane. The purpose of the tertiary or aromatic amine is to catalyze the reaction and neutralize hydrochloric or hydroiodic acid formed in the reaction. Typical of amines which can be used are triethylamine, triisopropylamine, pyridine and imidazole. In a preferred embodiment of this step, mesitylenesulfonyl chloride is reacted with the starting material in the presence of triethylamine in tetrahydrofuran at $-20°$ to $0°$ C.

In the next step of the process the enol sulfonate, enol ether or enol benzoate is reacted under an inert atmosphere and in an inert solvent with an excess of a metallic hydride reducing agent capable of reducing the ester and carbonyl groups on the enol sulfonate, ether or benzoate to primary and secondary alcohol groups respectively. Typical hydride reducing agents useful in this step are sodium bis(2-methoxymethoxy) aluminum hydride, sodium borohydride, lithium aluminum hydride and lithium borohydride. A preferred reducing agent is sodium bis(2-methoxymethoxy) aluminum hydride sold under the trade name Red-al ® by the Aldrich Chemical Company of Milwaukee, Wis. This step of the reaction, which should be carried out at a temperature of no greater than about 35° C. results in reduction of the carbonyl and ester groups on the starting material to hydroxyl groups. In a preferred embodiment of this step, the reducing agent is added to the reaction mass while maintaining the reaction mass at a temperature not in excess of about $-70°$ C. to convert the carbonyl group to hydroxyl and then raising the reaction mass to a temperature of from about $-20°$ to about $0°$ C. to convert the ester group to hydroxyl. This two step procedure is preferred over the single step process because fewer side reactions, and therefore greater yields, result.

The next process step involves adding a dilute aqueous solution of a mineral acid and a water immiscible organic solvent to the reaction mass. This step converts unreacted amine to its amine salt and forms two layers, i.e., an aqueous layer and an organic layer with the amine salt residing in the aqueous layer. The addition of an acid also serves to quench excess reducing agent. Alternatively, the reducing agent can be quenched by the addition of concentrated aqueous sodium potassium tartrate or a carboxylic acid, e.g., acetic acid, before the addition of the mineral acid.

At this point, the aqueous phase containing the amine salt and the organic phase containing the intermediate phase material formed previously are separated and the organic phase is washed with an aqueous base to remove any remaining acid therefrom. Typical of aqueous bases which may be used are aqueous sodium or potassium hydroxide, carbonate or bicarbonate. Saturated sodium bicarbonate is preferred. This is an essential step in the process because acid contaminants may interfere and prevent the next step in the process from occurring.

At this point the intermediate material is separated from the organic phase by well known techniques such as evaporation of the solvent, preferentially at reduced pressure. The isolated intermediate material is dissolved in chloroform, methylene chloride, a lower alcohol or a mixture thereof and reacted with sodium oxalate and oxalic acid to form the desired product. A preferred solvent for this step is chloroform containing about 10% methanol or 10% ethanol.

Preferred amounts of reagents for this step are two parts of sodium oxalate by weight to one part of oxalic acid for three parts of the 2-(ω-carboalkoxyalkyl)-4R,4S or 4RS-hydroxycyclopentan-1,3-dione as basic starting material several steps previous.

Upon formation of the desired product, it is separated from the reaction mass and reacted with an organolithiocuprate as previously described to form the desired carbinol analogue of PGE₁.

The preparation of 2-(7-hydroxyheptyl)-4R-hydroxycyclopent-2-enone is illustrated by Examples I and II.

EXAMPLE I

A solution of 11.9 g (46.6 mmol) of 2-(6-carbomethoxyhexyl)-4R-hydroxy-cyclopentan-1,3-dione:

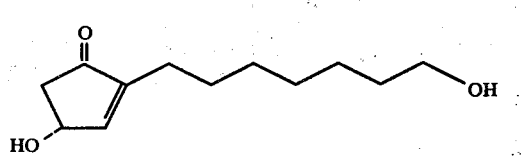

in 125 ml of dry tetrahydrofuran (THF) was stirred at −10° C. under argon while 14.3 ml (102.2 mmol) of triethylamine was added dropwise. A solution of 10.25 g (46.8 mmol) of mesitylenesulfonyl chloride in 75 ml of dry THF was then added dropwise with stirring at −10° to 0° C. over 45 minutes. After another 15 minutes the ice bath was removed and the reaction was stirred without cooling for 1 hour. The resultant reaction mixture was filtered through dry Celite into a solution of 50.3 g (174 mmol) of Red-al ® (70% in benzene) in 75 ml of dry THF and stirred at −20° to −10° C. under nitrogen. This addition was carried out over a period of 1.25 hours. The resultant mixture was then stirred at −10° to −5° C. for 3 hours whereupon it was quenched by the dropwise addition of a solution of 20 ml of acetic acid in 30 ml of THF. The resultant mixture was stirred for 0.5 hours at 0° C. and then diluted with 1 liter of ether. A 500 ml portion of 10% aqueous hydrochloric acid was added, and the resultant mixture was stirred until all of the solids had dissolved whereupon the phases were separated and the aqueous phase was extracted with ether several times. The combined extracts and original phase were washed with saturated aqueous sodium bicarbonate, dried (MgSO₄) and evaporated in vacuo. The yield of yellow residue was 17.0 g. This residue was dissolved in 500 ml of chloroform and stirred overnight under argon with 4.5 g of oxalic acid (hydrate) and 8.1 g of sodium oxalate. The resultant mixture was washed with saturated aqueous sodium bicarbonate and the wash solution was back extracted with ether whereupon the combined extract was dried (Na₂SO₄) and evaporated in vacuo. The residue was chromatographed on silicic acid-Celite (80:20) using benzene-ethyl acetate gradients to yield 1.5 g (15%) of pure 2-(7-hydroxyheptyl)-4R-hydroxycyclopent-2-enone.

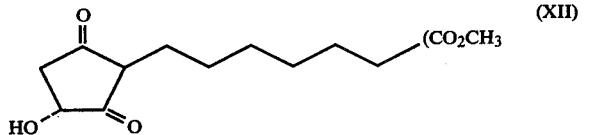

The structure of this material was confirmed by nuclear magnetic resonance, infrared and mass spectral analysis with the following results:

NMR (CDCl₃); δ0.8–1.9 (1 OH, broad m); 2.2 (2H, broad m); 2.26 (1H, d of d, J=2.5; 10Hz); 2.82 (1H, d of d, J=6, 19Hz); 3.6 (2H, broad t, J=6Hz); 4.03 (2H, s); 4.9 (1H, m); and 7.2 ppm (1H, broad s). IR (CHCl₃); 1030, 1710, 2860, 2930, 3005, 3200–3550 (broad) and 3600 cm⁻¹. UV max (CH₃OH): 223 mm (e 8,300). Mass Spectrum (70 eV)m/e: 213, 212 (parent), 194, 168, 149, 135, 122, 95, 82, 81, 69, 67, 55, 43 (base), and 41. $[\alpha]^{25}$: +18.16 (c1.0, CH₃OH); +12.7 (c1.09, CHCl₃).

EXAMPLE II

A solution of 26.7 g (104 mmol) of XII in 225 ml of dry THF was stirred at 0° C. under argon as 29 ml (209 mmol) of dry triethylamine was added followed by a solution of 22.9 g (104 mmol) of mesitylenesulfonyl chloride in 70 ml of dry THF added dropwise over 15 minutes. The resultant mixture was stirred at 0° C. for 1 hour and then without cooling for 1 hour. The resultant brown mixture was added over 0.5 hour to a stirred solution of 166 gm of Red-al ® in 300 ml of dry THF under argon with −78° C. bath cooling. The resultant mixture was stirred for 0.5 hour at −78° C. and then allowed to come to −10° C. over 1 hour whereupon it was stirred at −10° C. to 0° C. for 2 hours. At this point, the resultant mixture was stirred at 0° C. as 60 ml of acetic acid was slowly added dropwise. The resultant mixture was diluted with 2 liters of ether and then 1 liter of 10% aqueous hydrochloric acid was added dropwise. The resultant mixture was stirred thoroughly whereupon the phases were separated and the aqueous phase extracted with ethyl acetate. At this point, the combined organic phase and extract was washed with brine and then saturated aqueous sodium bicarbonate, dried (MgSO₄) and evaporated in vacuo. The residue was dissolved in a mixture of 1 liter of chloroform, 50 ml of ethanol, 20 g of sodium oxalate and 10 g of oxalic acid (hydrate) with the resulting mixture being stirred under argon for 15 hours. At this point, the resultant mixture was washed with saturated sodium bicarbonate and the wash solution back-extracted twice with chloroform. The combined extracts were dried (MgSO₄) and evaporated in vacuo to yield 37 g of a residue which was chromatographed on silica gel 60 using ethyl acetate elution to yield 10.2 g (46.2%) of pure product the analysis of which was identical to that obtained in Example I and by earlier analyses of the desired product.

The 4S or 4RS material is prepared in a similar manner using the appropriate starting material.

The following disclosure illustrates the conversion of the material prepared in Example I to 1,11α,15R-trihydroxy-16,20-methanoprost-13E-en-9-one of the formula:

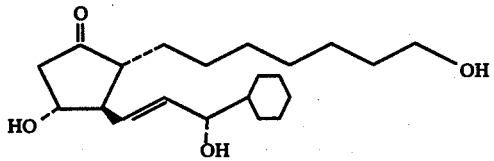

A. Blocking of Substituted Cyclopent-2-enone

A mixture of 1.174 g of the 2-(7-hydroxyheptyl)-4R-hydroxycyclopent-2-enone prepared in Example I, 2.25 ml of dihydropyran, 10 mg of toluenesulfonic acid hydrate and 20 ml of dry ether were stirred under nitrogen at ambient temperature for 1.5 hours to give a clear solution and then stirred for an additional 2.5 hours. The reaction mixture was diluted with ether and then washed with saturated aqueous sodium bicarbonate whereupon the wash solution was back-extracted with ether. The combined extract was dried (Na$_2$SO$_4$) and evaporated in vacuo to yield 2.7 g of 2-[7-tetrahydropyran-2-yloxy)-heptyl]-4$^R$-(tetrahydropyran-2-yloxy)cyclopent-2-enone.

B. Preparation of 1-Chloro-3-Cyclohexylprop-1E-en-3-one.

Acetylene was passed sequentially through an aluminum oxide trap, two concentrated (98%) sulfuric acid traps and an empty trap. A 2-liter, 3-necked flask was then filled with an atmosphere of the acetylene through one sidearm using a glass tube and adaptor. Carbon tetrachloride (614 ml) was then added to the flask whereupon the flask was cooled by an external ice-water bath and additional acetylene was bubbled in for several minutes. The central neck of the flask was fitted with a stirrer and the remaining sidearm was fitted with a condensor. The gas addition tube was removed from the reaction flask and 368 g of aluminum chloride was added to the carbon tetrachloride. Acetylene was again bubbled through the reaction mixture whereupon the gas addition tube was replaced by an addition funnel which contained 327 g of cyclohexanecarboxylic acid chloride. That solution was slowly added to the stirred reaction mixture whereupon the addition funnel was replaced by the gas addition tube and the acetylene addition was continued for 4 hours while the reaction was stirred and cooled. The reaction mixture was then poured over a mixture of 3500 g of ice and 1500 ml of saturated brine in a large beaker. The phases of the resultant mixture were then separated, and the aqueous phase was extracted three times with ether. The combined organic phases were washed with 10% aqueous hydrochloric acid and then with saturated aqueous sodium bicarbonate. They were dried on anhydrous CaCl$_2$ and evaporated in vacuo (vacuum pump) to yield crude material which was then distilled (0.1 mm) to give 210 g of pure product (bp 92°–95° C.) which had the following spectral properties: nmr (CDCl$_3$)δ0.9–2.8 (11H), 6.7 (1H, d, J=14Hz), and 7.40 ppm (1H, d, J=14Hz).

Part of this material was used in the following reaction.

C. Preparation of 1-Iodo-3-Cyclohexylprop-1E-3-one.

A solution of 40 g of 1-chloro-3-cyclohexylprop-1E-en-3-one and 182 g of sodium iodide in 200 ml of dry acetone (distilled from anhydrous potassium carbonate) was refluxed under argon for 18 hours. The solvent was then removed by evaporation in vacuo whereupon the residue was mixed with water and extracted two times with methylene chloride. The combined extract was dried over anhydrous CaCl$_2$ and then evaporated in vacuo to yield 57.3 g of the desired compound which was purified by chromatography on silica gel using chloroform elution to yield 56.8 g of pure material which had the following spectral properties: nmr (CDCl$_3$)δ0.9–2.8 (11H, m), 7.30 (1H, d, J=15Hz) and 7.92 ppm (1H, d, J=15Hz).

All of the above product was mixed with 36.2 g of an earlier batch and used below:

D. Preparation of 1-Iodo-3-Cyclohexyl-3RS-Hydroxyprop-1E-ene.

A solution of 93.0 g of 1-iodo-3-cyclohexylprop-1E-en-3-one in 400 ml of absolute ethanol was stirred with cooling (−10° C.) as 14.0 g of sodium borohydride dissolved in 125 ml absolute ethanol was added. After addition of the borohydride was complete, the reaction mixture was stirred (1.5 hours at 0° C.). Solvent was removed by evaporation in vacuo. The residue was mixed with brine and extracted with ether whereupon the combined extracts were dried over anhydrous MgSO$_4$ and then evaporated in vacuo to yield 92.4 g of the desired compound which had the following spectral properties: nmr (CDCl$_3$)δ0.8–2.4 (11H, m), 3.0 (1H, s), 3.86 (1H, t, J=5.5 Hz), 6.28 (1H, d, J=14.5Hz), and 6.67 ppm (1H, d of d, J=14.5, 6.0Hz); ir (CHCl$_3$) 3600, 3450 (broad), 1600, 1450, 1000 and 953 cm$^{-1}$.

All of the above material was used below.

E. 1-Iodo-3-Cyclohexyl-3RS-(1-Ethoxyethoxy)prop-1E-ene.

A mixture of 4.4 g of 1-iodo-3-cyclohexyl-3RS-hydroxyprop-1E-ene, 30 ml of ethyl vinyl ether and one drop of phosphorous oxychloride were stirred overnight (16 hours) at ambient temperature under argon. The resultant mixture was poured into saturated aqueous sodium bicarbonate and extracted several times with ether. The combined extracts were washed with brine, dried (MgSO$_4$) and evaporated in vacuo to yield the title compound which was then purified by chromatography on silica gel using chloroform elution.

Preparation of
[3-Cyclohexyl-3RS-(1-Ethoxyethoxy)prop-1E-en-1-yl]-Pent-1-yn-1-yl)-Lithiocuprate Hexamethylphosphorous Triamide.

A solution of 1.1 g (3.0 mmol) of 1-iodo-3-cyclohexyl-3RS-(1-ethoxyethoxy-prop)1E-ene in 15 ml of ether was stirred at −78° C. under argon atmosphere and 4.0 ml (6.8 mmol) of t-butyllithium (1.7 M in pentane) was added dropwise by a syringe. After stirring for 2 hours at −78° C., a solution of 0.4 g (3.1 mmol) of copper (I) pentyne solubilized with 0.84 ml of hexamethylphosphoroustriamide in 10 ml of ether slowly was added to form the desired organometallic reagent.

Preparation of 1,11α,15R and S-trihydroxy-16,20 methanoprost-13E-en-9-one.

A solution of 1.15 g (3.0 mmol) of 2-[7-(tetrahydropyran-2-yloxy)heptyl]-4R-(tetrahydropyran-2-yloxy)cyclopent-2-enone in 5 ml of dry ether was slowly added to the organometallic reagent prepared as above at −78° C. The resultant slurry was stirred for 30 minutes at −78° C. and then 90 minutes at −20° C. The reaction was quenched at −20° C. by the addition of 20% aqueous ammonium sulfate followed by addition of 2% aqueous sulfuric acid to acidify the aqueous phase. The resultant mixture was shaken thoroughly and then filtered through infusion earth (Celite). Filtrate phases were separated, and the organic phase was washed with brine and subsequently with saturated aqueous NaHCO$_3$. The organic phase was dried over anhydrous sodium sulfate and evaporated in vacuo. The residue was stirred with 25 ml of acetic acid-water-tetrahydrofuran (65:35:10) for 20 hours under argon. The resultant solution was evaporated in vacuo to remove solvent, and the residue was dissolved in ethyl acetate and washed with saturated aqueous NaHCO$_3$. The wash solution was extracted twice with ethyl acetate and the combined extract dried over anhydrous magnesium sulfate and then evaporated in vacuo. The resultant oil was chromatographed on silicic acid-Celite using a benzene-ethyl acetate gradient elution to yield 105.6 mg of the more polar 15R prostaglandin (A):

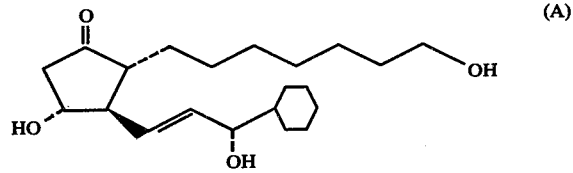
(A)

and 83.1 mg of the less polar 15S prostaglandin (B):

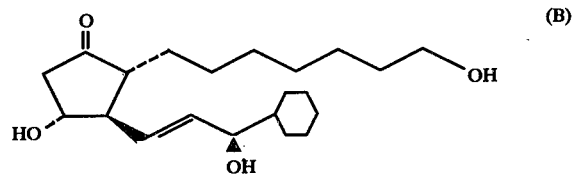
(B)

as light yellow oils. The nmr, ir and mass spectra of the 15R and 15S forms, which were identical, are as follows: nmr (CDCl$_3$); δ0.7–2.7 (27H, complex); 3.2–4.4 (7H, complex); and 5.6 ppm (2H, m); ir (film): 970, 2940 and 3200–2700 cm$^{-1}$ (broad). Mass spectrum (70 eV) m/e: no parent at 352, but strong 334 (p-H$_2$O), 316 (p-2H$_2$O), 290, 269, 263, 251, 233, 197, 179, 163, 161, 150, 135, 121, 111, 109, 107 and others below 100. [α]$_D^{25}$: −76.5° C. (15R, c2.0, CHCl$_3$). Calculated: 3, 71.84; H, 10.31. Found: C, 6916; H, 10.31.

Compound A, above, i.e., the 15R isomer, was found to be highly effective in inhibition of gastric secretion in the rat using a procedure based on that described by Lipman, W. (J. Pharm. Pharmacol., 21:335[1967].

What is claimed is:

1. A process for the preparation of 2-(ω-hydroxyalkyl)-4R,4S or 4RS-hydroxy-cyclopent-2-enone corresponding to the formula:

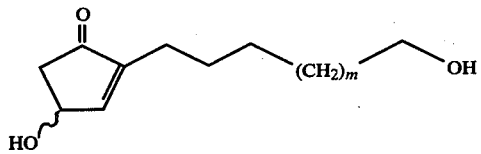

wherein m is an integer of from 2 to 4, which process comprises the steps of:

A. reacting in an inert solvent under a dry atmosphere a 2-(ω-carboalkoxyalkyl)-4R,4S or 4RS-hydroxycyclopentan-1,3-dione corresponding to the formula:

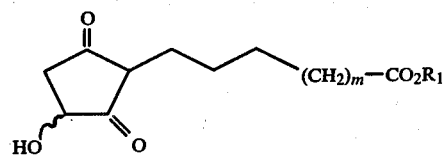

wherein m is an integer of from 2 to 4 and R$_1$ is an alkyl group containing from 1 to 4 carbon atoms, with mesitylenesulfonyl chloride, a lower alkyliodide of from 1 to 4 carbon atoms or benzoyl chloride in the presence of an excess of a tertiary or aromatic amine to convert the starting material to the corresponding enol sulfonate, enol ether or enol benzoate;

B. reacting in an inert solvent and under an inert atmosphere the so-formed enol sulfonate, enol ether or enol benzoate with an excess of a metallic hydride reducing agent capable of reducing the ester and carbonyl group on the enol sulfonate, ether or benzoate to primary and secondary alcohol groups respectively, at a temperature not in excess of about 35° C. to reduce the carbonyl group on the starting material to a hydroxyl group and to reduce the ester group on the starting material to an alcohol group to thereby form an intermediate material corresponding to the formula:

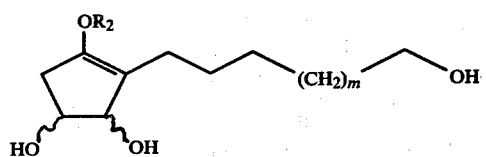

wherein R$_2$ is mesitylenesulfonyl, lower alkyl or benzoyl and m is an integer from 2 to 4;

C. adding a dilute aqueous solution of a mineral acid and a water immiscible organic solvent to the reaction mass to convert unreacted amine to its corresponding amine salt and cause the amine salt to reside in the so-formed aqueous phase and cause the intermediate material formed in step B to reside in the so-formed organic phase;

D. separating the aqueous phase from the organic phase;

E. washing the organic phase with an aqueous base to remove the acid therefrom;

F. separating the intermediate material formed in step B from the organic phase; and G. dissolving the intermediate material in chloroform, methylene chloride, a lower alcohol or a mixture thereof and reacting it with sodium oxalate and oxalic acid to form the desired product.

2. The process of claim 1 wherein the reducing agent in step B is sodium bis(2-methoxyethoxy) aluminum hydride or sodium borohydride.

3. The process of claim 1 wherein the aqueous base used in step E is saturated sodium bicarbonate.

4. The process of claim 1 wherein a protic material is added to the reaction mass after step B to quench the excess hydride reducing agent.

5. The process of claim 1 wherein the lower alcohol in step G is ethanol.

6. The process of claim 1 wherein m is 3 and $R_1$ is methyl.

7. The process of claim 1 wherein the amine in step A is a tertiary amine.

8. The process of claim 7 wherein the tertiary amine is triethylamine.

9. The process of claim 1 wherein the starting dione is reacted in step A with mesitylenesulfonyl chloride to form the corresponding enol sulfonate.

10. The process of claim 4 wherein the protic material is a carboxylic acid or concentrated aqueous sodium potassium tartrate.

11. The process of claim 1 wherein the mineral acid added in step C is hydrochloric or sulfuric acid.

12. The process of claim 1 wherein the intermediate material is dissolved in chloroform in step F.

13. The process of claim 12 wherein the chloroform is mixed with methanol or ethanol.

14. The process of claim 1 wherein in step B the hydride reducing agent is initially added to the reaction mass at a temperature of about −70° C. to reduce the carbonyl group on the starting material to a hydroxyl group and then the temperature of the reaction mass is raised to a temperature of from about −20° to about 0° C. to cause the ester group on the starting material to be reduced to an alcohol group.

15. The process of claim 1 wherein the starting material is 2(ω-carboalkoxyalkyl)-4R-hydroxycyclopentan-1,3-dione and the product is 2(ω-hydroxyalkyl)-4R-hydroxycyclopent-2-enone.

16. The process of claim 1 wherein the starting material is 2(ω-carboalkoxyalkyl)-4RS-hydroxycyclopentan-1,3-dione and the product is 2(ω-hydroxyalkyl)-4RS-hydroxycyclopent-2-enone.

17. A process for the preparation of 2-(ω-hydroxyalkyl-4R, 4S or 4RS-hydroxycyclopent-2-enone corresponding to the formula

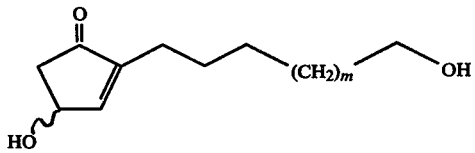

wherein m is an integer of from 2 to 4 which process comprises the steps of:

A. reacting in an inert solvent under a dry atmosphere a 2-(ω-carboalkoxyalkyl)-4R,4S or 4RS-hydroxycyclopentan-1,3-dione corresponding to the formula:

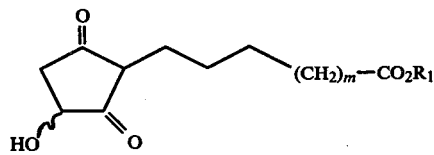

wherein m is an integer of from 2 to 4 and $R_1$ is an alkyl group containing from 1 to 4 carbon atoms with mesitylenesulfonyl chloride in the presence of an excess of triethylamine to convert the starting material to its enol mesitylenesulfonate;

B. reacting in an inert solvent and under an inert atmosphere the so-formed enol mesitylenesulfonate with an excess of sodium bis (2-methoxyethoxy)aluminum hydride at a temperature not in excess of about −70° C. to thereby form a material corresponding to the formula:

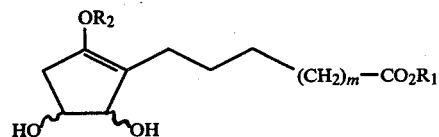

wherein $R_2$ is mesitylenesulfonyl;

C. raising the temperature of the reaction mass to a temperature of from about −20° to about 0° C. to cause the ester group on the starting material to be reduced to an alcohol group and thereby form an intermediate material corresponding to the formula:

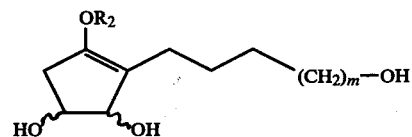

D. adding a dilute aqueous solution of hydrochloric acid and diethyl ether to the reaction mass to convert unreacted triethylamine to its amine salt and cause the amine salt to reside in the so-formed aqueous phase and the intermediate material formed in step C to reside in the so-formed organic phase;

E. separating the aqueous phase from the organic phase;

F. washing the organic phase with an aqueous sodium bicarbonate solution;

G. separating the intermediate material formed in step C from the organic phase; and H. dissolving the intermediate material in a mixture of chloroform and ethanol or methanol and reacting it with sodium oxalate and oxalic acid to form the desired product.

18. The process of claim 17 wherein m=3.

19. The process of claim 18 wherein $R_1$ is methyl.

20. The process of claim 17 wherein a carboxylic acid or concentrated aqueous sodium potassium tartrate is added to the reaction mass after step B to quench the excess sodium bis (2-methoxyethoxy) aluminum hydride.

21. The process of claim 20 wherein a carboxylic acid is added and the carboxylic acid is acetic acid.

22. The process of claim 17 wherein the chloroform used in step H is mixed with about 10% methanol or 10% ethanol.

23. The process of claim 17 wherein the starting material is 2-(ω-carboalkoxyalkyl)-4R-hydroxycyclopentan-1,3-dione and the product is 2-(ω-hydroxyalkyl)-4R-hydroxycyclopent-2-enone.

24. The process of claim 17 wherein the starting material is 2-(ω-carboxyalkoxyalkyl)-4S-hydroxycyclopentan-1,3-dione and the product is 2-(ω-hydroxyalkyl)-4S-hydroxycyclopent-2-enone.

25. The process of claim 17 wherein the starting material is 2-(ω-carboxyalkoxyalkyl)-4RS-hydroxycyclopentan-1,3-dione and the product is 2-(ω-hydroxyalkyl)-4RS-hydroxycyclopent-2-enone.

* * * * *

UNITED STATES PATENT AND TRADEMARK OFFICE
CERTIFICATE OF CORRECTION

PATENT NO. : 4,159,998
DATED : July 3, 1979
INVENTOR(S) : Harold C. Kluender

It is certified that error appears in the above-identified patent and that said Letters Patent are hereby corrected as shown below:

| | | |
|---|---|---|
| Column 1, | Line 59, | Change "net" to --nat--. |
| Column 1, | Line 65, | Delete the "(" |
| Column 1, | Line 66, | Change " then " to -- when --. |
| Column 3, | Lines 30-35, | Delete the formula and numeral and insert: |

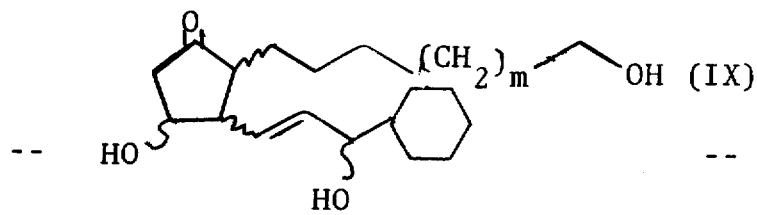

| | | |
|---|---|---|
| Column 5, | Line 12, | Change "(ω-carboalkoxyalkyl" to -- (ω-carboalkoxyalkyl) --. |

UNITED STATES PATENT AND TRADEMARK OFFICE
CERTIFICATE OF CORRECTION

PATENT NO. : 4,159,998
DATED : July 3, 1979    Page 2 of 2
INVENTOR(S) : Harold C. Kluender It is certified that error appears in the above-identified patent and that said Letters Patent are hereby corrected as shown below:

| | | |
|---|---|---|
| Column 6, | Line 14, | insert a -- comma (,) --- after the word " atmosphere". |
| Column 6, | Line 39, | Change "(2-methoxymethoxy)" to -- (2-methoxyethoxy) --. |
| Column 6, | Line 42, | Change "(2-methoxymethoxy)" to -- (2-methoxyethoxy) --. |
| Column 7, | Line 37, | Delete the "(" from the formula. |

Signed and Sealed this

Twenty-seventh Day of November 1979

[SEAL]

Attest:

RUTH C. MASON
Attesting Officer

LUTRELLE F. PARKER
Acting Commissioner of Patents and Trademarks